United States Patent
Lai et al.

(10) Patent No.: US 10,361,074 B2
(45) Date of Patent: Jul. 23, 2019

(54) IONIZATION CHAMBER HAVING A POTENTIAL-WELL FOR ION TRAPPING AND ION COMPRESSION

(71) Applicant: Rapiscan Systems, Inc., Torrance, CA (US)

(72) Inventors: Hanh T. Lai, Arlington, MA (US); Karl Goedecke, Everett, MA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 15/820,331

(22) Filed: Nov. 21, 2017

(65) Prior Publication Data

US 2018/0182604 A1    Jun. 28, 2018

Related U.S. Application Data

(60) Provisional application No. 62/439,580, filed on Dec. 28, 2016.

(51) Int. Cl.
| | | |
|---|---|---|
| *H01J 49/06* | (2006.01) | |
| *H01J 49/26* | (2006.01) | |
| *G01N 27/62* | (2006.01) | |

(52) U.S. Cl.
CPC .......... *H01J 49/065* (2013.01); *G01N 27/622* (2013.01); *H01J 49/061* (2013.01); *H01J 49/26* (2013.01)

(58) Field of Classification Search
CPC ......... H01J 49/065; H01J 49/061; H01J 49/26
USPC ........................................ 250/281, 282, 283
See application file for complete search history.

(56) References Cited

U.S. PATENT DOCUMENTS

| | | |
|---|---|---|
| 5,491,337 A | 2/1996 | Jenkins |
| 6,211,516 B1 | 4/2001 | Syage |
| 6,326,615 B1 | 12/2001 | Syage |
| 6,329,653 B1 | 12/2001 | Syage |

(Continued)

FOREIGN PATENT DOCUMENTS

| | | |
|---|---|---|
| AT | 303589 T | 9/2005 |
| AT | 480769 T | 9/2010 |

(Continued)

OTHER PUBLICATIONS

International Search Report for PCT/US17/62888, dated Feb. 16, 2018.

*Primary Examiner* — Nicole M Ippolito
(74) *Attorney, Agent, or Firm* — Novel IP

(57) ABSTRACT

An ionization chamber. The ionization chamber includes a vessel, an ionization source, an ion gate, and a mid-ring electrode. The vessel defines an ionization region. The vessel includes a first end axially disposed opposite a second end. The ionization source is located at the first end and generates ions. The ion gate is located at the second end of the vessel. The mid-ring electrode is located between the ionization source and the ion gate. During an ion compression stage, the ionization source is charged to a first ionization source potential, the ion gate is charged to a first ion gate potential, and the mid-ring electrode is charged to a first mid-ring potential that is less than the first ionization source potential and the first ion gate potential. The first mid-ring potential is configured to generate a potential well proximate the mid-ring electrode. The ions collect at the potential well.

21 Claims, 5 Drawing Sheets

(56) References Cited

U.S. PATENT DOCUMENTS

| | | |
|---|---|---|
| 6,630,664 B1 | 10/2003 | Syage |
| 6,642,513 B1 | 11/2003 | Jenkins |
| 6,690,005 B2 | 2/2004 | Jenkins |
| 6,708,572 B2 | 3/2004 | Jenkins |
| 6,737,642 B2 | 5/2004 | Syage |
| 6,765,198 B2 | 7/2004 | Jenkins |
| 6,815,670 B2 | 11/2004 | Jenkins |
| 6,831,273 B2 | 12/2004 | Jenkins |
| 6,840,122 B1 | 1/2005 | Jenkins |
| 7,047,829 B2 | 5/2006 | Napoli |
| 7,071,465 B2 | 7/2006 | Hill, Jr. |
| 7,109,476 B2 | 9/2006 | Hanold |
| 7,119,342 B2 | 10/2006 | Syage |
| 7,141,786 B2 | 11/2006 | McGann |
| 7,161,144 B2 | 1/2007 | Syage |
| 7,196,325 B2 | 3/2007 | Syage |
| 7,253,727 B2 | 8/2007 | Jenkins |
| 7,299,710 B2 | 11/2007 | Syage |
| 7,338,638 B2 | 3/2008 | McGann |
| 7,401,498 B2 | 7/2008 | Syage |
| 7,448,248 B2 | 11/2008 | Carey |
| 7,456,393 B2 | 11/2008 | Napoli |
| 7,528,367 B2 | 5/2009 | Haigh |
| 7,541,577 B2 | 6/2009 | Davenport |
| 7,594,422 B2 | 9/2009 | Perry |
| 7,594,447 B2 | 9/2009 | Napoli |
| 7,663,099 B2 | 2/2010 | Reda |
| 7,721,588 B2 | 5/2010 | Perry |
| 7,829,841 B2 | 11/2010 | Bateman |
| 7,856,898 B2 | 12/2010 | Carey |
| 7,880,137 B2 | 2/2011 | McGann |
| 8,161,830 B2 | 4/2012 | Boudries |
| 8,186,234 B2 | 5/2012 | Syage |
| 8,288,735 B2 | 10/2012 | Syage |
| 8,402,842 B2 | 3/2013 | Syage |
| 8,434,375 B1 | 5/2013 | Syage |
| 8,614,582 B2 | 12/2013 | Syage |
| 8,686,355 B2 | 4/2014 | Patterson |
| 8,723,111 B2 | 5/2014 | Syage |
| 8,857,278 B2 | 10/2014 | Syage |
| 8,866,073 B2 | 10/2014 | Goedecke |
| 8,952,327 B2 | 2/2015 | Patterson |
| 9,063,086 B1 | 6/2015 | Garimella |
| 9,147,565 B1 | 9/2015 | Goedecke |
| 9,354,153 B2 | 5/2016 | Syage |
| 9,482,655 B2 | 11/2016 | Vilkov |
| 9,528,969 B2 | 12/2016 | Shaw |
| 9,558,924 B2 | 1/2017 | Syage |
| 9,683,981 B1 | 6/2017 | Vilkov |
| 9,689,857 B1 | 6/2017 | Vilkov |
| 9,726,655 B2 | 8/2017 | Syage |
| 9,766,218 B2 | 9/2017 | Lai |
| 9,789,434 B1 | 10/2017 | Lai |
| 2003/0089846 A1* | 5/2003 | Cooks ............ H01J 49/0013 250/281 |
| 2009/0045334 A1* | 2/2009 | Ding ............... H01J 49/0481 250/288 |
| 2015/0048246 A1 | 2/2015 | Green |
| 2015/0221489 A1 | 8/2015 | Wollnik |
| 2016/0282304 A1 | 9/2016 | Vilkov |
| 2017/0103880 A1 | 4/2017 | Syage |
| 2017/0213715 A1 | 7/2017 | Davila |
| 2017/0261483 A1 | 9/2017 | Vilkov |
| 2017/0261484 A1 | 9/2017 | Vilkov |
| 2017/0284977 A1 | 10/2017 | Rogers |
| 2017/0309463 A1 | 10/2017 | Vilkov |
| 2018/0158665 A1 | 6/2018 | Eiceman |
| 2018/0164189 A1 | 6/2018 | Bilodeau |
| 2018/0172635 A1 | 6/2018 | Lai |
| 2018/0172650 A1 | 6/2018 | Platow |
| 2018/0182603 A1 | 6/2018 | Schmidt |
| 2018/0182604 A1 | 6/2018 | Lai |
| 2018/0283993 A1 | 10/2018 | Shaw |
| 2018/0284081 A1 | 10/2018 | Shaw |
| 2018/0356320 A1 | 12/2018 | Romanov |
| 2019/0011421 A1 | 1/2019 | Rogers |

FOREIGN PATENT DOCUMENTS

| | | |
|---|---|---|
| CA | 2153371 C | 3/1999 |
| CA | 2436256 C | 6/2007 |
| CA | 2382823 C | 11/2007 |
| CA | 2362449 C | 10/2008 |
| CA | 2411532 C | 4/2010 |
| CA | 2285153 C | 5/2010 |
| CA | 2479875 C | 2/2011 |
| CA | 2538709 C | 2/2013 |
| CA | 2790430 A1 | 3/2013 |
| CA | 2807894 A1 | 9/2013 |
| CA | 2620405 C | 7/2014 |
| CA | 2548177 C | 9/2014 |
| CA | 2844222 A1 | 9/2014 |
| CA | 2845959 A1 | 9/2014 |
| CA | 2688352 C | 6/2015 |
| CA | 2644937 C | 11/2015 |
| CA | 2904479 A1 | 3/2016 |
| CA | 2910780 A1 | 4/2016 |
| CA | 2913931 A1 | 6/2016 |
| CA | 2915785 A1 | 6/2016 |
| CA | 2924580 A1 | 9/2016 |
| CA | 2647651 C | 11/2016 |
| CA | 2738053 C | 5/2017 |
| CA | 2959791 A1 | 9/2017 |
| CA | 2959796 A1 | 9/2017 |
| CA | 2962154 A1 | 9/2017 |
| CA | 2964147 A1 | 10/2017 |
| CN | 100445767 C | 12/2008 |
| CN | 103308590 A | 9/2013 |
| CN | 105738461 A | 7/2016 |
| CN | 107037114 A | 8/2017 |
| CN | 107167334 A | 9/2017 |
| CN | 107167335 A | 9/2017 |
| CN | 107271254 A | 10/2017 |
| DE | 69528418 T2 | 1/2003 |
| DE | 69926965 T2 | 6/2006 |
| EP | 2368102 A2 | 9/2011 |
| EP | 2637013 A2 | 9/2013 |
| EP | 2778650 A2 | 9/2014 |
| EP | 2778669 A1 | 9/2014 |
| EP | 2884254 A1 | 6/2015 |
| EP | 3015858 A1 | 5/2016 |
| EP | 3032570 A2 | 6/2016 |
| EP | 3040717 A1 | 7/2016 |
| EP | 1938078 B1 | 3/2017 |
| EP | 1297554 B1 | 4/2017 |
| EP | 3182111 A1 | 6/2017 |
| ES | 2183855 | 4/2003 |
| FR | 692712 A | 11/1930 |
| GB | 992782 A | 5/1965 |
| GB | 2075578 A | 11/1981 |
| GB | 2496286 A | 5/2013 |
| GB | 2536076 A | 9/2016 |
| JP | 3045655 B2 | 5/2000 |

\* cited by examiner

IONIZATION CHAMBER HAVING A POTENTIAL-WELL FOR ION TRAPPING AND ION COMPRESSION

PRIORITY

This application claims the benefit of priority to U.S. Provisional Patent Application No. 62/439,580 filed on Dec. 28, 2016 entitled "IONIZATION CHAMBER HAVING A POTENTIAL-WELL FOR ION TRAPPING AND ION COMPRESSION," which is hereby incorporated by reference herein in its entirety.

BACKGROUND

The field of the disclosure relates generally to ion mobility spectrometer (IMS) systems and, more particularly, to an ionization chamber having a potential-well for ion trapping and ion compression.

At least other some known spectrometry detection devices include ion mobility spectrometer (IMS), such as, for example, an ion trap mobility spectrometer (ITMS). Many of the known ITMS detection systems include a collection device that collects particulate, liquid, and/or gaseous samples from an object of interest. The samples are channeled to an ionization chamber that includes an ionizing source that ionizes the sample to form positive ions, negative ions, and free electrons. The ionization chamber in ITMS detection systems is typically a field-free region. As the ions are generated in the ionization chamber to increase the ion population therein, a retaining grid, or gate, is maintained at a slightly greater potential than the electric field in the ionization chamber to induce a retention field and reduce the potential for ion leakage from the chamber. Thus, the ions are "trapped" within the ionization chamber or ionization region. An electric field is then induced across the ionization chamber and, depending on the polarity of the induced electric field, the positive ions or the negative ions are pulsed from the ionization chamber, through a high-voltage "kick-out pulse," into a drift region through the retaining grid. The ions of the opposite polarity are attracted to the walls of the ionization chamber and are discharged there.

In some ITMS detection systems, the drift region includes a plurality of sequential, annular electrodes. A collector electrode is positioned on the opposite side of the drift region from the ionization chamber and is held at a ground potential. For those systems that use negative ions, the annular electrodes are energized to voltages that are sequentially less negative between the ionization chamber and the collector electrode, thereby inducing a constant positive field. Motion is induced in the negative ions from the initial pulse in the ionization chamber and the ions are channeled through the drift region to the collector electrode. Signals representative of the ion population at the collector electrode are generated and transmitted to an analysis system to determine the constituents in the collected samples.

The population of ions is pulsed into the drift region from the ionization chamber typically in the form of an ion disk with a predetermined axial width value and possibly a trailing ion tail. As the disk of ions traverses the drift region, high-mobility analytes separate from low-mobility analytes induces expansion and distortion of the ion disk. The high-mobility analytes form a disk that transits faster than a disk formed of low-mobility analytes and the disks may overlap as they are received at the collector electrode. The peaks on the trace thus generated on the spectral analysis equipment are distorted with poor resolution and are difficult to analyze.

Moreover, in many ITMS detection systems, there is no precise control over the width of the ion disk injected into the drift region. Fundamentally, this is due to inconsistent, and sometimes, incomplete clearing out of the ionization chamber due to non-homogeneity of the electric field induced in the ionization chamber, e.g., low field regions at the back of the ionization chamber.

SUMMARY

In one aspect, an ionization chamber is provided. The ionization chamber includes a vessel, an ionization source, an ion gate, and a mid-ring electrode. The vessel defines an ionization region. The vessel includes a first end axially disposed opposite a second end. The ionization source is located at the first end and generates ions. The ion gate is located at the second end of the vessel. The mid-ring electrode is located between the ionization source and the ion gate. During an ion compression stage, the ionization source is charged to a first ionization source potential, the ion gate is charged to a first ion gate potential, and the mid-ring electrode is charged to a first mid-ring potential that is less than the first ionization source potential and the first ion gate potential. The first mid-ring potential is configured to generate a potential well proximate the mid-ring electrode. The ions collect at the potential well.

Optionally, said ion gate is further configured to be charged to the first ion gate potential to prevent the ions from traveling through said ion gate and from said vessel.

Optionally, said ionization source is further configured to be charged to the first ionization source potential to evacuate the ions from the first end of said vessel.

Optionally, the first ionization source potential is equal to the first ion gate potential.

Optionally, during a release stage: said ionization source is further configured to be charged to a second ionization source potential that is greater than the first ionization source potential; said mid-ring electrode is further configured to be charged to a second mid-ring potential that is greater than the first mid-ring potential; and said ion gate further configured to be charged to a second ion gate potential that is less than the second mid-ring potential and the second ionization source potential, wherein the second mid-ring potential and the second ion gate potential are configured to cooperate to move a pulse of the ions through said ion gate and from said second end of said vessel. Optionally, during the release stage, a difference between the second ionization source potential and the second mid-ring potential is less than a difference between the second mid-ring potential and the second ion gate potential.

Optionally, said mid-ring electrode is further configured to be charged to a potential gradient over an axial dimension of said mid-ring electrode. Optionally, the potential gradient is axially asymmetrical.

Optionally, said ion gate comprises a conductive grid disposed between the ionization region and a drift region.

In another aspect, a method of compressing ions is provided. The method includes generating ions at an ionization source within an ionization chamber. The method includes charging a mid-ring electrode to a first mid-ring potential to generate a potential well relative to a first ionization source potential and a first ion gate potential, the potential well configured to collect the ions. The method includes charging an ion gate to the first ion gate potential to prevent the ions from traveling through the ion gate and into a drift region.

Optionally, the method further comprises charging the ionization source to the first ionization source potential, wherein the first ionization source potential and the first ion gate potential are greater than the first mid-ring potential. Optionally, the method further comprises: charging the mid-ring electrode to a second mid-ring potential that is greater than the first mid-ring potential; and charging the ion gate to a second ion gate potential that is less than the second ionization source potential and the second mid-ring potential to pulse the ions into the drift region. Optionally, the second ion gate potential is equal to the first ion gate potential. Optionally, the second ionization source potential and the second mid-ring potential are greater than the second ion gate potential, such that a pulse of the ions travel through the ion gate.

Optionally, charging the mid-ring electrode to the first mid-ring potential comprises charging the mid-ring electrode with a potential gradient over a length of the mid-ring electrode in an axial dimension of the ionization chamber.

In yet another aspect, an ion mobility spectrometer (IMS) device is provided. The IMS device includes a drift tube and an ionization chamber. The ionization chamber includes an ionization source, an ion gate, and a mid-ring electrode. The drift tube defines a drift region therein. The ionization chamber defines an ionization region therein. The ionization source is located at a first end of the ionization region and is configured to generate ions. The ionization source is configured to be charged to a first ionization source potential during an ion compression stage. The ion gate is located adjacent to the drift tube and at a second end of the ionization region. The ion gate is configured to be charged to a first ion gate potential during the ion compression stage. The mid-ring electrode is located between the ionization source and the ion gate. The mid-ring electrode is configured to be charged, during the ion compression stage, to a first mid-ring potential that is less than the first ionization source potential and the first ion gate potential. The first mid-ring potential is configured to generate a potential well, proximate the mid-ring electrode, where the ions collect during the ion compression stage.

Optionally, during a release stage: said ionization source is further configured to be charged to a second ionization source potential that is greater than the first ionization source potential; said mid-ring electrode is further configured to be charged to a second mid-ring potential that is greater than the first mid-ring potential; and said ion gate is further configured to be charged to a second ion gate potential that is less than the second ionization source potential and the second mid-ring potential, wherein the second ionization source potential, the second mid-ring potential, and the second ion gate potential are configured to cooperate to move a pulse of the ions through said ion gate and into said drift region.

Optionally, during the release stage, a difference between the second ionization source potential and the second mid-ring potential is less than a difference between the second mid-ring potential and the second ion gate potential.

Optionally, said mid-ring electrode is further configured to be charged to a potential gradient over an axial dimension of said mid-ring electrode.

Optionally, said ion gate is further configured to be charged to the first ion gate potential to prevent the ions from traveling through said ion gate and into said drift region.

Optionally, said ionization source is further configured to be charged to the first ionization source potential to evacuate the ions from the first end of said ionization region.

Optionally, said ion gate comprises a Bradbury-Nielson gate.

The aforementioned and other embodiments of the present specification shall be described in greater depth in the drawings and detailed description provided below.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

Figure 1:
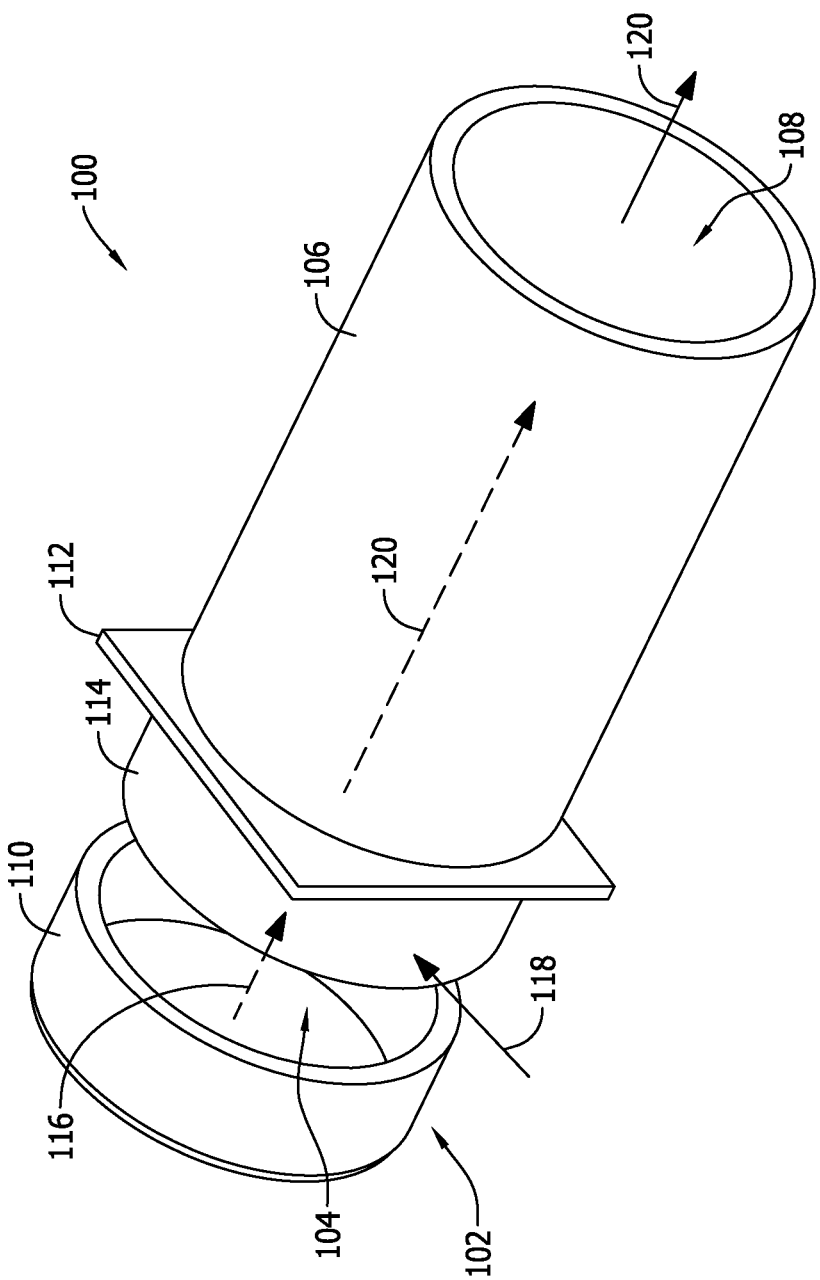
FIG. 1 is a perspective diagram of an exemplary ion mobility spectrometry device.

Unless otherwise indicated, the drawings provided herein are meant to illustrate features of embodiments of this disclosure. These features are believed to be applicable in a wide variety of systems comprising one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, a number of terms are referenced that have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged. Such ranges are identified and include all the sub-ranges contained therein unless context or language indicates otherwise.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

Embodiments of the IMS systems described herein provide an ionization chamber having one or more mid-ring electrodes. More specifically, the mid-ring electrode is charged to a low potential to generate a potential well within the ionization chamber. The potential well operates to collect ions during a compression stage such that, during a release stage, a higher-density pulse of ions is released into a drift region in which detection is carried out. The potential well is further configured to be charged relative to a potential of the ionization source and a potential of the ion gate. The potentials of the ionization source, mid-ring electrode, and the ion gate cooperate to move ions away from the ionization source during compression and release. The potentials of the ionization source, mid-ring electrode, and the ion gate further cooperate to collect the ions near the ion gate in a higher-density than in a field-free ionization region. The potentials of the mid-ring electrode and the ion gate are configured to increase the density of ions during compression without allowing ions to travel through the ion gate into the drift region. The increased density of ions results in a high-density pulse of ions released into the drift region, thus increasing the ion signal and improving detection performance.

FIG. 1 is a perspective diagram of an exemplary IMS device 100. IMS device 100 includes an ionization chamber 102, within which an ionization region 104 is defined, coupled to a drift tube 106, within which a drift region 108 is defined. Ionization chamber 102 generally includes a vessel within which an ionization source 110 is located, at a first end of ionization chamber 102, and within which an ion gate 112 is located, at a second end of ionization chamber 102. Ionization chamber 102 includes a mid-ring electrode 114 located between ionization source 110 and ion gate 112.

During a compression stage, ionization source 110 generates ions 116 that are mixed with a sample 118 that is injected into ionization chamber 102. During a release stage, a pulse of ions 120 is released through ion gate 112 and into drift region 108.

Ion gate 112, in certain embodiments, includes a conductive grid or mesh material that is charged as an electrode. Such an embodiment having a conductive grid is referred to as an ion trap mobility spectrometer (ITMS) device. In alternative embodiments, ion gate 112 includes a Bradbury-Nielson gate. The Bradbury-Nielson gate includes two sets of alternating wires that are charged to an equal potential during the release stage. The potential of the two sets of alternating wires is less than the potential of ionization source 110 and higher than the potential of drift region 104 during the release stage. During ion compression, the potential of one set of alternating wires is offset relative to the potential of the second set of alternating wires. Such potentials prevent ions near the gate from traveling through ion gate 112 and into drift region 104 by causing the ions to collide with the sets of alternating wires. During the ion compression stage, the first mid-ring potential is less than the first ionization source potential and the first ion gate two wires' potential.

Figure 2:
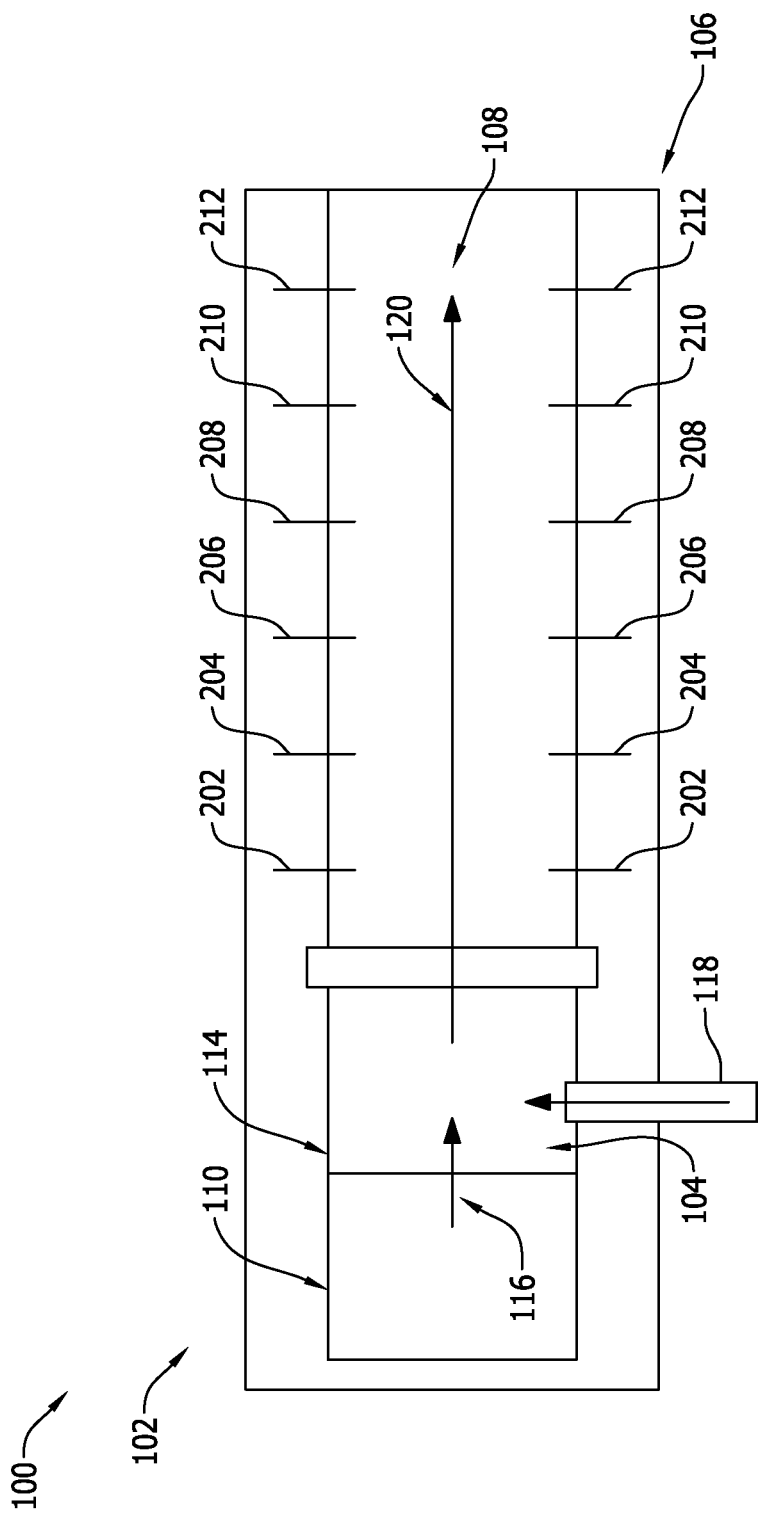
FIG. 2 is a cross-sectional diagram of the ion mobility spectrometry device shown in FIG. 1.

FIG. 2 is a cross-sectional diagram of ITMS device 100, shown in FIG. 1. FIG. 2 illustrates ionization chamber 102 and drift region 108. During the compression stage, ions 116 are generated by ionization source 110 and mixed with sample 118 in ionization region 104. Mid-ring electrode 114 is charged to a lower potential than ionization source 110 and ion gate 112 to generate a potential well within ionization region 104. Ions 116 collect in the potential wells in a narrow band near ion gate 112. During the release stage, pulse 120 of ions 116 travels through ion gate 112 and into drift region 108.

Drift tube 106 includes a series of electrodes 202, 204, 206, 208, 210, and 212 axially disposed along the length of drift tube 106. Electrodes 202, 204, 206, 208, 210, and 212 are charged to respective potentials to generate a flow of pulse 120 of ions 116 from ion gate 112 through drift region 108.

Figure 3:
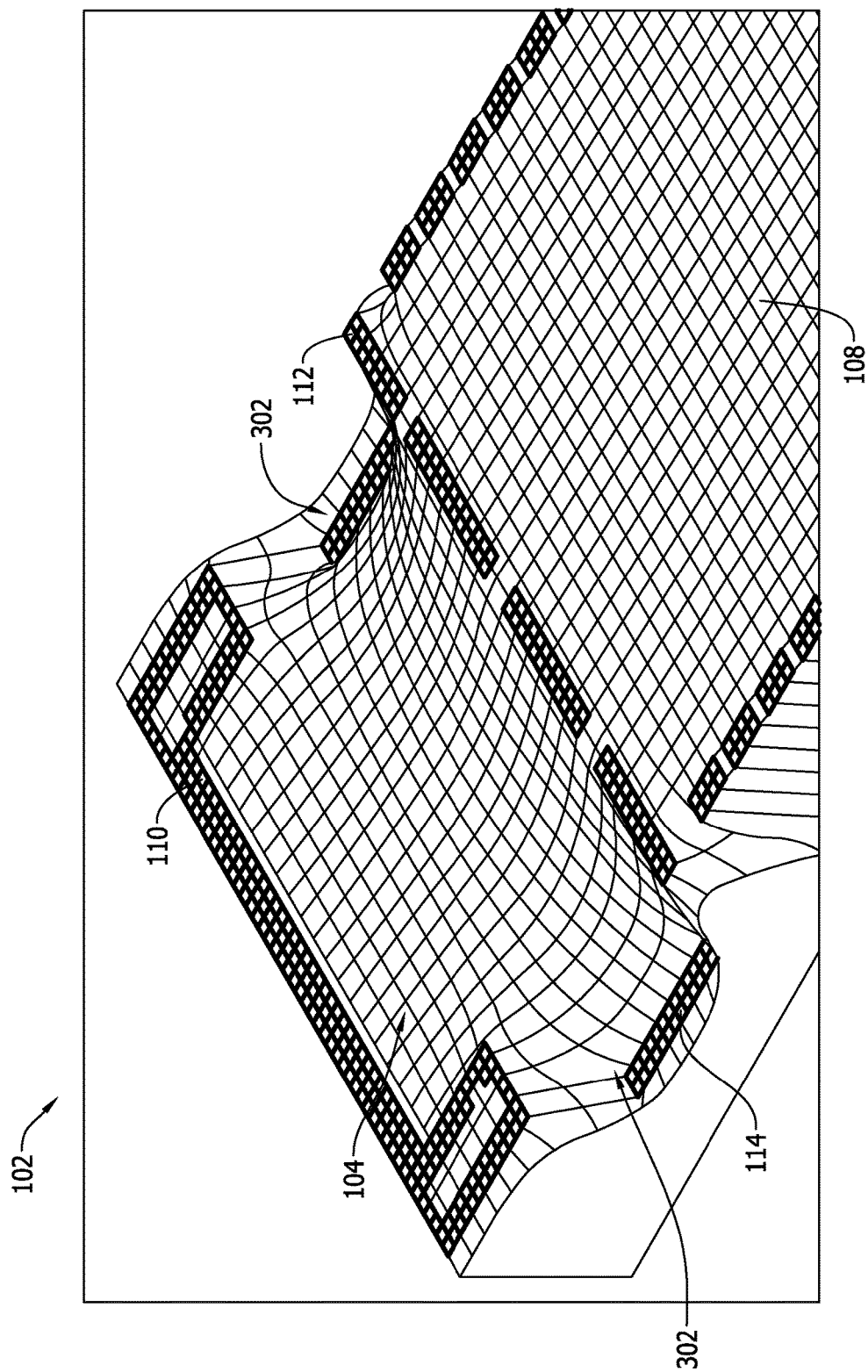
FIG. 3 is a potential diagram of the ionization chamber shown in FIGS. 1 and 2 during a compression stage.
Figure 4:
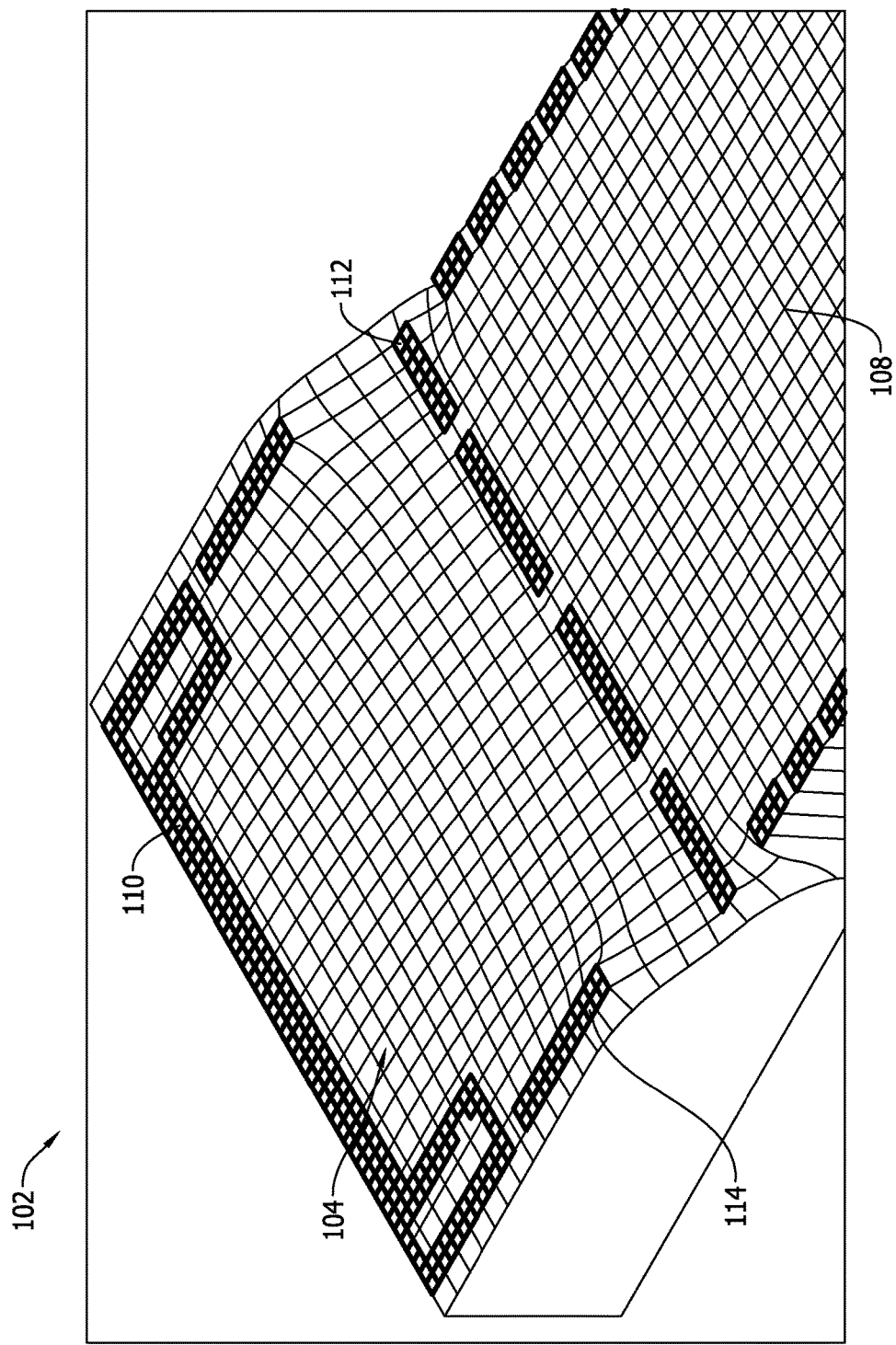
FIG. 4 is a potential diagram of the ionization chamber shown in FIGS. 1 and 2 during a release stage.

FIGS. 3 and 4 are potential diagrams of ionization chamber 102, shown in FIGS. 1 and 2. FIG. 3 is a potential diagram during the compression stage, and FIG. 4 is a potential diagram during the release stage. The potential diagrams of FIGS. 3 and 4 illustrate potentials at ionization source 110, ion gate 112, mid-ring electrode 114, and drift region 108.

Referring to FIG. 3, mid-ring electrode 114 is charged to be at a lower potential than ionization source 110 and ion gate 112. The low potential of mid-ring electrode 114 generates a potential well 302 in which generated ions collect. More specifically, the potential of ionization source 110 relative to potential well 302 results in ions moving away from ionization source 110 toward ion gate 112. The potential of ion gate 112 relative to potential well 302 results in the ions collecting near ion gate 112, but far enough from ion gate 112 that ions do not travel, or "leak," through ion gate 112 into drift region 108. The potential difference between potential well 302 and ionization source 110 and the potential difference between potential well 302 and ion gate 112 may range from ten volts to several hundred volts, depending on the specific implementation. Generally, as the depth of potential well 302 increases, the so too does the ion concentration. However, the potentials at which ionization source 110, ion gate 112, and mid-ring electrode 114 are charged should be optimized to achieve a high concentration of ions in potential well 302 while still ensuring the ions have sufficient energy to be "kicked out" of potential well 302 during the release stage. Moreover, the potentials of ionization source 110 relative to ion gate 112 may be equal or offset, depending on the specific implementation. In certain embodiments, the potential of mid-ring electrode 114 is maintained at a potential gradient along the axial dimension of ionization region 104. The potential gradient, in certain embodiments, is symmetrical in the axial dimension, for example, forming a potential trough at an axial mid-point of potential well 302. In other embodiments, the potential gradient is asymmetrical in the axial dimension, for example, forming a potential trough nearer ion gate 112 relative to the axial mid-point. Potential well 302 collects a high-density population of ions near ion gate 112. In such embodiments, mid-ring electrode 114 may be composed of a semiconductor material to control the potential gradient.

Referring to FIG. 4, which illustrates potentials of ionization chamber 102 during the release stage, ionization source 110 and mid-ring electrode 114 are charged to a higher potential than ion gate 112 and drift region 108. In certain embodiments, potentials of ionization source 110 and mid-ring electrode are equal or offset with respect to each other, while still at a higher potential than ion gate 112. In certain embodiments, the potential of ion gate 112 is equal during both the compression stage and the release stage. Generally, such potential enable a pulse of ions to move from ionization chamber 104, through ion gate 112, and into drift region 108. The release of a pulse of ions through ion gate 112 is enabled by lowering the potential of ion gate 112, or "pulsing" ion gate 112, for a pulse duration, after which the potential of ion gate 112 is increased to resume trapping ions in ionization region 104. The potential of ionization source 110, in certain embodiments, is greater than the potential of mid-ring electrode 114. In alternative embodiments, ionization source 110 and mid-ring electrode 114 are charged to an equal potential or slightly offset. For example, ionization source 110 may be offset by plus-or-minus 10 volts relative to mid-ring electrode 114. Such offset, or the potential difference between ionization source 110 and mid-ring electrode 114, is less than the potential difference between mid-ring electrode 114 and ion gate 112. Such potentials ensure ions move from ionization region 104 into drift region 108 during the release stage.

Referring again to FIGS. 3 and 4, the high-density population of ions in potential well 302 during the compression stage enables a high concentration of ions to pulse through ion gate 112 during the release stage. Thus, a high-density pulse of ions travels from ion gate 112 and through drift region 108, improving the ion signal and further improving detection performance.

Figure 5:
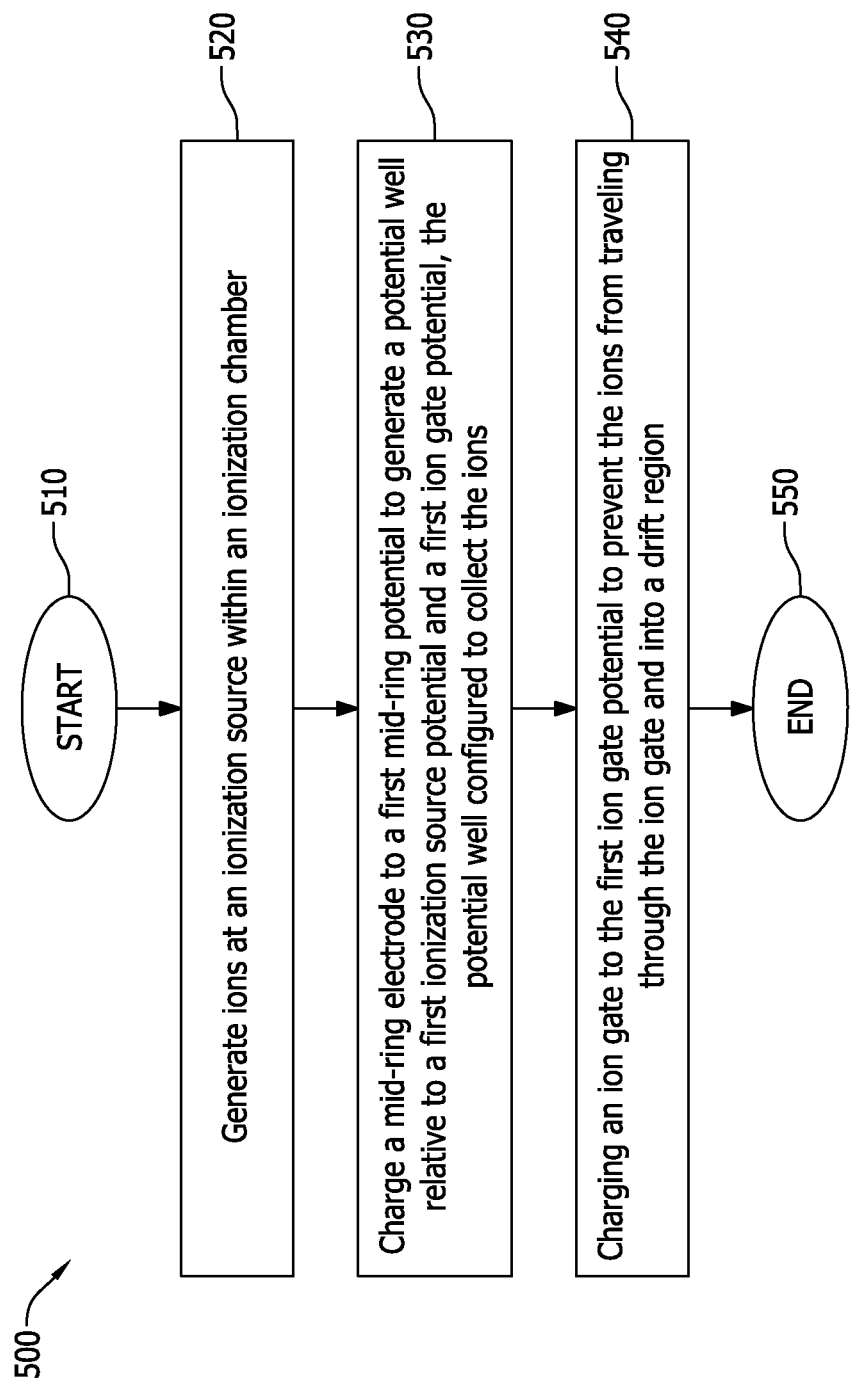
FIG. 5 is a flow diagram of an exemplary method of compressing ions in the ionization chamber shown in FIGS. 1 and 2.

FIG. 5 is a flow diagram of an exemplary method 500 of compressing ions ionization chamber 102, shown in FIGS. 1 and 2. Method 500 begins at a start step 510. Method 500 includes generating 520 ions 116 using ionization source 110 within ionization chamber 102. Mid-ring electrode 114 is charged 530 to a first mid-ring potential to generate potential well 302 relative to a first ionization source potential of ionization source 110 and a first ion gate potential of ion gate 112. Potential well 302 is configured to collect ions 116. Ion gate 112 is charged 540 to the first ion gate potential to prevent ions 116 from traveling through ion gate 112 and into drift region 108.

In certain embodiments, during the compression stage, ionization source 110 is charged to the first ionization source potential, where the first ionization source potential and the first ion gate potential are greater than the first mid-ring potential. Further, in certain embodiments, during the release stage, mid-ring electrode 114 is charged to a second mid-ring potential that is greater than the first mid-ring potential. Also during the release stage, ion gate 112 is charged to a second ion gate potential that is less than the first ion gate potential to pulse ions 116 into drift region 108. Method 500 terminates at an end step 550.

An exemplary technical effect of the methods, systems, and apparatus described herein includes at least one of: (a) generating a potential well into which ions collect before being pulsed into a drift region; (b) increasing an ion density in the potential well region during compression and in the pulse during release; (c) improving ion signal intensity for the pulse of ions during detection; (d) charging a mid-ring electrode within the ionization chamber with a potential gradient; (e) charging the ionization source, the mid-ring electrode, and the ion gate during compression to move ions away from the ionization source; (f) charging the ionization source, the mid-ring electrode, and the ion gate during compression to move ions toward the ion gate; and (g) charging the mid-ring electrode and the ion gate during compression to prevent ions from traveling through the ion gate.

Exemplary embodiments of methods, systems, and apparatus for dual source ionizers are not limited to the specific embodiments described herein, but rather, components of systems and/or steps of the methods may be utilized independently and separately from other components and/or steps described herein. For example, the methods may also be used in combination with other non-conventional ion trap mobility spectrometers, and are not limited to practice with only the systems and methods as described herein. Rather, the exemplary embodiment can be implemented and utilized in connection with many other applications, equipment, and systems that may benefit from increased efficiency, reduced operational cost, and reduced capital expenditure.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ionization chamber, comprising:
  a vessel within which an ionization region is defined, said vessel comprising a first end axially disposed opposite a second end;
  an ionization source located at said vessel's first end and configured to generate ions, said ionization source configured to have a first ionization source potential during an ion compression stage;
  an ion gate located at said second end and configured to have a first ion gate potential during the ion compression stage; and
  a mid-ring electrode located between said ionization source and said ion gate, said mid-ring electrode configured to have, during the ion compression stage, a first mid-ring potential that is less than the first ionization source potential and the first ion gate potential, the first mid-ring potential set at a value to generate a potential well proximate said mid-ring electrode.

2. The ionization chamber of claim 1, wherein said first ion gate potential is set at a value such that ions are prevented from traveling through said ion gate and from said vessel.

3. The ionization chamber of claim 1, wherein said first ionization source potential is set at a value such that ions are evacuated from the first end of said vessel.

4. The ionization chamber of claim 1, wherein the first ionization source potential is equal to the first ion gate potential.

5. The ionization chamber of claim 1, wherein, during a release stage:
said ionization source is further configured to have a second ionization source potential that is greater than the first ionization source potential;
said mid-ring electrode is further configured to have a second mid-ring potential that is greater than the first mid-ring potential; and
said ion gate further configured to have a second ion gate potential that is less than the second mid-ring potential and the second ionization source potential, wherein the second mid-ring potential and the second ion gate potential cooperate to move a pulse of the ions through said ion gate and from said second end of said vessel.

6. The ionization chamber of claim 5, wherein, during the release stage, a difference between the second ionization source potential and the second mid-ring potential is less than a difference between the second mid-ring potential and the second ion gate potential.

7. The ionization chamber of claim 1, wherein said mid-ring electrode is further configured to have a potential gradient over an axial dimension of said mid-ring electrode.

8. The ionization chamber of claim 7, wherein the potential gradient is axially asymmetrical.

9. The ionization chamber of claim 1, wherein said ion gate comprises a conductive grid disposed between the ionization region and a drift region.

10. A method of compressing ions, said method comprising:
generating ions at an ionization source within an ionization chamber;
charging a mid-ring electrode to a first mid-ring potential to generate a potential well relative to a first ionization source potential and a first ion gate potential, wherein the potential well is configured to collect the ions;
charging an ion gate to the first ion gate potential to prevent the ions from traveling through the ion gate and into a drift region, wherein the mid-ring electrode is located between the ionization source and the ion gate; and
charging the ionization source to the first ionization source potential, wherein the first ionization source potential and the first ion gate potential are greater than the first mid-ring potential.

11. The method of claim 10 further comprising:
charging the mid-ring electrode to a second mid-ring potential that is greater than the first mid-ring potential; and
charging the ion gate to a second ion gate potential that is less than the second ionization source potential and the second mid-ring potential to pulse the ions into the drift region.

12. The method of claim 11, wherein the second ion gate potential is equal to the first ion gate potential.

13. The method of claim 11, wherein the second ionization source potential and the second mid-ring potential are greater than the second ion gate potential, such that a pulse of the ions travel through the ion gate.

14. A method of compressing ions, said method comprising:
generating ions at an ionization source within an ionization chamber;
charging a mid-ring electrode to a first mid-ring potential to generate a potential well relative to a first ionization source potential and a first ion gate potential, wherein the potential well is configured to collect the ions and wherein charging the mid-ring electrode to the first mid-ring potential comprises charging the mid-ring electrode with a potential gradient over a length of the mid-ring electrode in an axial dimension of the ionization chamber;
charging an ion gate to the first ion gate potential to prevent the ions from traveling through the ion gate and into a drift region, wherein the mid-ring electrode is located between the ionization source and the ion gate.

15. An ion mobility spectrometer (IMS) device, comprising:
a drift tube defining a drift region therein; and
an ionization chamber defining an ionization region therein, said ionization chamber comprising:
an ionization source located at a first end of said ionization region and configured to generate ions, said ionization source configured to have a first ionization source potential during an ion compression stage;
an ion gate located adjacent to said drift tube and at a second end of said ionization region, said ion gate configured to have a first ion gate potential during the ion compression stage; and
a mid-ring electrode located between said ionization source and said ion gate, said mid-ring electrode configured to have, during the ion compression stage, a first mid-ring potential that is less than the first ionization source potential and the first ion gate potential, the first mid-ring potential configured to generate a potential well, proximate said mid-ring electrode, where the ions collect during the ion compression stage.

16. The IMS device of claim 15, wherein, during a release stage:
said ionization source is further configured to have a second ionization source potential that is greater than the first ionization source potential;
said mid-ring electrode is further configured to have a second mid-ring potential that is greater than the first mid-ring potential; and
said ion gate is further configured to have a second ion gate potential that is less than the second ionization source potential and the second mid-ring potential, wherein the second ionization source potential, the second mid-ring potential, and the second ion gate potential cooperate to move a pulse of the ions through said ion gate and into said drift region.

17. The IMS device of claim 16, wherein, during the release stage, a difference between the second ionization source potential and the second mid-ring potential is less than a difference between the second mid-ring potential and the second ion gate potential.

18. The IMS device of claim 15, wherein said mid-ring electrode is further configured to have a potential gradient over an axial dimension of said mid-ring electrode.

19. The IMS device of claim 15, wherein said first ion gate potential is set at a value such that ions are prevented from traveling through said ion gate and into said drift region.

20. The IMS device of claim 15, wherein said first ionization source potential is set at a value such that ions are evacuated from the first end of said ionization region.

21. The IMS device of claim 15, wherein said ion gate comprises a Bradbury-Nielson gate.

* * * * *